US008318395B2

(12) United States Patent
Saitoh et al.

(10) Patent No.: US 8,318,395 B2
(45) Date of Patent: Nov. 27, 2012

(54) DIBENZOANTHRACENE COMPOUND AND ORGANIC LIGHT EMITTING DEVICE HAVING THE SAME

(75) Inventors: Akihito Saitoh, Yokohama (JP); Keiji Okinaka, Kawasaki (JP); Satoshi Igawa, Fujisawa (JP); Jun Kamatani, Tokyo (JP); Naoki Yamada, Inagi (JP); Masashi Hashimoto, Tokyo (JP); Masanori Muratsubaki, Hachioji (JP); Takao Takiguchi, Chofu (JP); Akihiro Senoo, Kawasaki (JP); Shinjiro Okada, Kamakura (JP); Minako Nakasu, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 323 days.

(21) Appl. No.: 12/293,409

(22) PCT Filed: Apr. 19, 2007

(86) PCT No.: PCT/JP2007/058990
§ 371 (c)(1),
(2), (4) Date: Sep. 17, 2008

(87) PCT Pub. No.: WO2007/123254
PCT Pub. Date: Nov. 1, 2007

(65) Prior Publication Data
US 2009/0079344 A1    Mar. 26, 2009

(30) Foreign Application Priority Data

Apr. 20, 2006  (JP) .................................. 2006-116903
Feb. 21, 2007  (JP) .................................. 2007-040900

(51) Int. Cl.
    *G03G 15/02*      (2006.01)
(52) U.S. Cl. ...................... 430/58.05; 428/690; 428/917
(58) Field of Classification Search .................. None
    See application file for complete search history.

(56) References Cited

U.S. PATENT DOCUMENTS

| 7,674,533 | B2 * | 3/2010 | Sakamoto et al. ............. 428/690 |
| 2002/0048688 | A1 | 4/2002 | Fukuoka et al. |
| 2004/0076853 | A1 | 4/2004 | Jarikov |
| 2005/0064233 | A1 * | 3/2005 | Matsuura et al. ............. 428/690 |
| 2007/0087223 | A1 | 4/2007 | Sakamoto et al. |
| 2007/0104977 | A1 * | 5/2007 | Arakane et al. ............... 428/690 |

FOREIGN PATENT DOCUMENTS

| JP | 2000-277262 | 10/2000 |
| JP | 2001-284050 | 10/2001 |
| JP | 2007-112729 | 5/2007 |
| WO | 2004/018588 A1 | 3/2004 |
| WO | WO 2008/078824 A1 | 7/2008 |

OTHER PUBLICATIONS

Duan et al., "Halogenations of Anthracenes and Dibenz[a,c]anthracene with N-Bromosuccinimide and N-Chlorosuccinimide", J. Org. Chem. (2000), 65:3006-9.
Abstract No. 58068, Chemical Abstracts, (1998) vol. 125.
Blum et al., "Tellurium-Mediated Halogen Transfer from Polyhaloalkanes to Diyne Acceptors", (1995) J. Org. Chem 60:4738-42.
L'Esperance et al., "A Study of Substituent Effects on Hydrogen-Arene Nonbonded Interactions", (1991) J. Org. Chem 56:688-94.
Smyth et al., "Synthesis of Longitudinally Twisted Polycyclic Aromatic Hydrocarbons via a Highly Substituted Aryne", (1990) J. Org. Chem. 55:1937-40.
'Mondal, et al., "Polycyclic Aromatic Compounds: A New Synthesis of Highly Arylated Quinones by Diels-Adler Reaction", (1984) Current Science, 53:1229-32.
Abstract No. 194595, (1984) Chemical Abstracts, vol. 99.
Grein et al., "Synthesen, ESR-und ENDOR-Untersuchungen hochverdrillter phenylsubstituierter Radikalanionen", (1981) Chemisch Berichter 114:254-66.
Konieczny, M. and Harvey, R.G., "Reductive Methylation of Polycyclic Aromatic Quinones", (1980) J. Org. Chem. 45:1308-10.
U.S. Appl. No. 12/296,058, Hiroki Ohrui, filed Dec. 12, 2007 National Stage Application.

* cited by examiner

*Primary Examiner* — Camie Thompson
(74) *Attorney, Agent, or Firm* — Fitzpatrick, Cella, Harper & Scinto

(57) ABSTRACT

Provided is a novel dibenzo[a,c]anthracene compound having substituents, which can be used in an organic light emitting device.

4 Claims, No Drawings

DIBENZOANTHRACENE COMPOUND AND ORGANIC LIGHT EMITTING DEVICE HAVING THE SAME

TECHNICAL FIELD

The present invention relates to a novel dibenzoanthracene compound and an organic light emitting device having the same.

BACKGROUND ART

Organic light emitting devices have been actively researched.

Japanese Patent Application Laid-Open No. 2001-284050 (paragraph 0013) suggests an anthracene derivative in which a monovalent residue of dibenzoanthracene is bonded to a substituted or unsubstituted, divalent anthracene residue.

In addition, U.S. Publication Application Publication No. 2004/0076853 (paragraph 1460) describes a dibenzoanthracene skeleton in a formula (W). Various substituents are listed for R1 to R14.

An organic compound for use in an organic light emitting device has been actively researched, and, furthermore, a search for a novel organic compound has been needed.

DISCLOSURE OF THE INVENTION

An object of the present invention is to provide an organic light emitting device using a dibenzo[a,c]anthracene derivative.

According to the present invention, there is provided a dibenzoanthracene compound represented by the following structural formla (I):

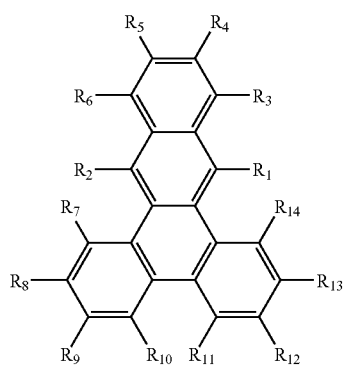

(I)

where:
$R_1$ and $R_2$ each represent a substituent;
the substituent includes any one of
a straight or branched alkyl group in which a hydrogen atom may be substituted by a fluorine atom,
a substituted or unsubstituted aryl group,
a substituted or unsubstituted heterocyclic group,
a substituted amino group, and
a halogen atom;
$R_3$ to $R_{14}$ each represent a hydrogen atom or a substituent; and
the substituent represented by any one of $R_3$ to $R_{14}$ includes any one of
a straight or branched alkyl group in which a hydrogen atom may be substituted by a fluorine atom,
a substituted or unsubstituted aryl group,
a substituted or unsubstituted heterocyclic group,
a substituted amino group, and
a halogen atom.

The compound of the present invention can be used as a host or guest for a light emitting layer in an organic electroluminescence (EL) device.

Further features of the present invention will become apparent from the following description of exemplary embodiments.

DESCRIPTION OF THE EMBODIMENTS

The present invention relates to a dibenzoanthracene compound represented by the following structural formula (I):

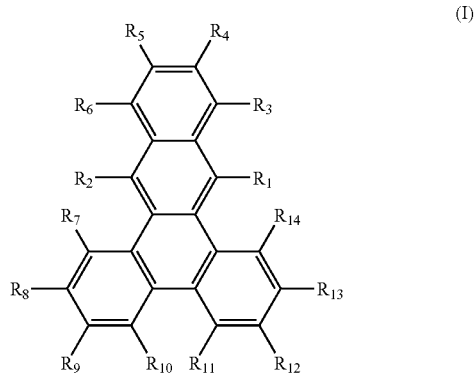

(I)

where:
$R_1$ and $R_2$ each represent a substituent;
the substituent includes any one of
a straight or branched alkyl group in which a hydrogen atom may be substituted by a fluorine atom,
a substituted or unsubstituted aryl group,
a substituted or unsubstituted heterocyclic group,
a substituted amino group, and
a halogen atom;
$R_3$ to $R_{14}$ each represent a hydrogen atom or a substituent; and
the substituent represented by any one of $R_3$ to $R_{14}$ includes any one of
a straight or branched alkyl group in which a hydrogen atom may be substituted by a fluorine atom,
a substituted or unsubstituted aryl group,
a substituted or unsubstituted heterocyclic group,
a substituted amino group, and
a halogen atom.

In addition, furthermore, the dibenzoanthracene compound represented by the above structural formula (I) is preferably a dibenzoanthracene compound represented by the following structural formula (II):

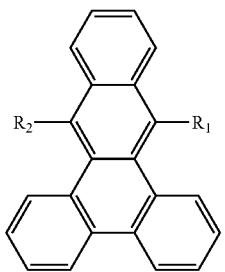
(II)

where:
R₁ and R₂ each represent a substituent; and
the substituent includes any one of
a straight or branched alkyl group in which a hydrogen atom may be substituted by a fluorine atom,
a substituted or unsubstituted aryl group,
a substituted or unsubstituted heterocyclic group,
a substituted amino group, and
a halogen atom.

Hereinafter, the present invention will be described in detail.

Examples of an alkyl group include a methyl group, an ethyl group, a normal propyl group, an isopropyl group, a normal butyl group, a tertiary butyl group, an octyl group, a cyclohexyl group, and a trifluoromethyl group. Examples of an alkoxy group include a methoxy group, an ethoxy group, a tertiary butyloxy group, and a trifluoromethyloxy group.

Examples of the aryl groups include a phenyl group, a biphenyl group, a terphenyl group, a fluorenyl group, a naphthyl group, a fluoranthenyl group, an anthryl group, a phenanthryl group, a pyrenyl group, a tetracenyl group, a pentacenyl group, a triphenylenyl group, and a perylenyl group.

Examples of the heterocyclic group include a thienyl group, a pyrrolyl group, a pyridyl group, an oxazolyl group, an oxadiazolyl group, a thiazolyl group, and a thiadiazolyl group. Examples of the substituted amino group include a dimethylamino group, a diethylamino group, a dibenzylamino group, a diphenylamino group, a ditolylamino group, and a dianisolylamino group.

Examples of the halogen atom include fluorine, chlorine, bromine, and iodine.

Specific examples of substituents of R₁ and R₂ include: alkyl groups such as a methyl group, an ethyl group, a normal propyl group, an isopropyl group, a normal butyl group, a tertiary butyl group, an octyl group, a cyclohexyl group, and a trifluoromethyl group; alkoxyl groups such as a methoxyl group, an ethoxyl group, a tertiary butyloxy group, and a trifluoromethyloxy group; aryl groups such as a phenyl group, a biphenyl group, a terphenyl group, a fluorenyl group, a naphthyl group, a fluoranthenyl group, an anthryl group, a phenanthryl group, a pyrenyl group, a tetracenyl group, a pentacenyl group, a triphenylenyl group, and a perylenyl group; heterocyclic groups such as a thienyl group, a pyrrolyl group, a pyridyl group, an oxazolyl group, an oxadiazolyl group, a thiazolyl group, and a thiadiazolyl group; and halogen atoms such as fluorine, chlorine, bromine, and iodine.

Of those substituents of $R_1$ and $R_2$ aryl groups such as a phenyl group, a biphenyl group, a terphenyl group, a fluorenyl group, a naphthyl group, a fluoranthenyl group, an anthryl group, a phenanthryl group, a pyrenyl group, a tetracenyl group, a pentacenyl group, a triphenylenyl group, and a perylenyl group; heterocyclic groups such as a pyridyl group, an oxazolyl group, an oxadiazolyl group, a thiazolyl group and a thiadiazolyl group; and fluorine are preferable.

Examples of a substituent that may be contained in the substituent of $R_1$ and $R_2$ include: alkyl groups such as a methyl group, an ethyl group, and a propyl group; aryl groups such as a phenyl group and a biphenyl group; heterocyclic groups such as a thienyl group, a pyrrolyl group, and a pyridyl group; amino groups such as a dimethylamino group, a diethylamino group, a dibenzylamino group, a diphenylamino group, a ditolylamino group, and a dianisolylamino group; and halogen atoms such as fluorine, chlorine, bromine, and iodine.

Of those, alkyl groups such as a methyl group, an ethyl group, and a propyl group, aryl groups such as a phenyl group and a biphenyl group, and fluorine are preferable.

In addition, $R_1$ and $R_2$ represented in the structural formula (I), in other words, 9- and 14-positions of dibenzo[a,c]anthracene establish a positional relationship electronically identical to that between 9- and 10-positions of anthracene.

In general, each of 9- and 10-positions of anthracene has high reactivity, and is easily oxidized.

Oxidation or reduction occurs in an organic light emitting device.

The inventors of the present invention have noticed that, when a dibenzoanthracene compound is used in an organic light emitting device, bonding a substituent except a hydrogen atom to any one of those positions of dibenzoanthracene is effective. That is, providing any one of those positions with not a hydrogen atom but a substituent can weaken the reactivity of the compound, specifically, can prevent oxidation. The inventors of the present invention have noticed that the stability of the organic light emitting device can be improved as a result of the prevention.

In addition, dibenzo[a,c]anthracene has a planar molecule. The probability that an excimer is produced is high because an interaction between the molecules of dibenzo[a,c]anthracene is so strong that the molecules are apt to be stacked. A molecule of dibenzo[a,c]anthracene preferably has a substituent to suppress the foregoing phenomenon. An aryl group having a high oscillator strength is preferably introduced to such position as described above.

Substituents at 9- and 14-positions of dibenzo[a,c]anthracene may be different from each other; the substituents are preferably identical to each other because the synthesis of an intermediate becomes simple, and the simple synthesis is advantageous in terms of cost.

Specific examples of the dibenzoanthracene compound according to the present invention are shown below.

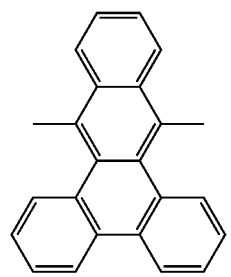
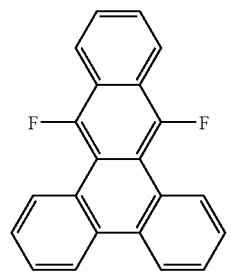
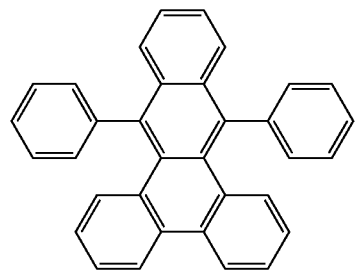
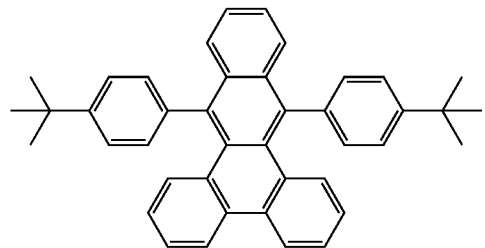
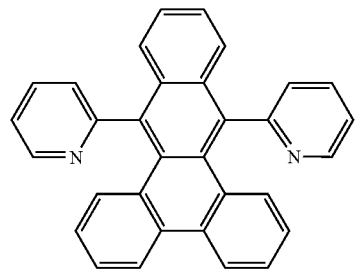
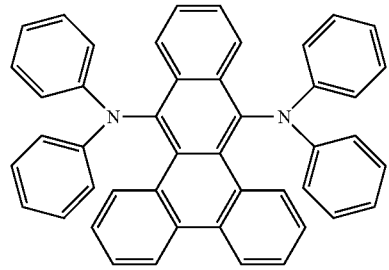
A1
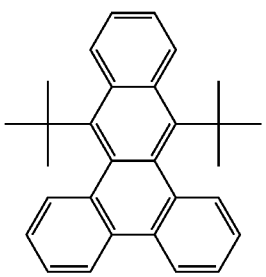
A2
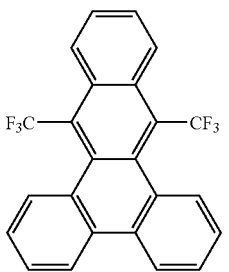
A3
A4
A7
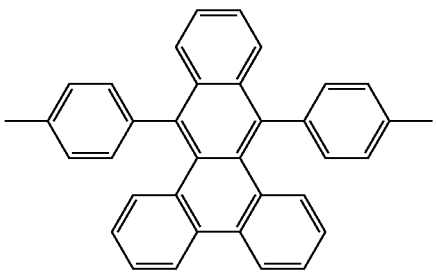
A8
A9
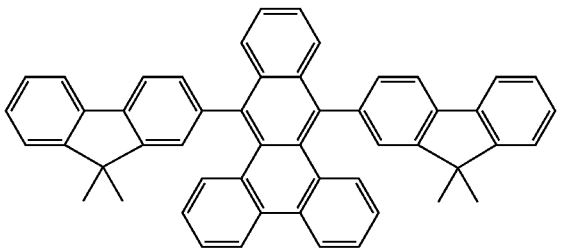
A10
A11
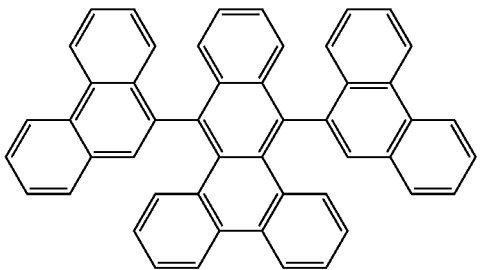
A12
A13
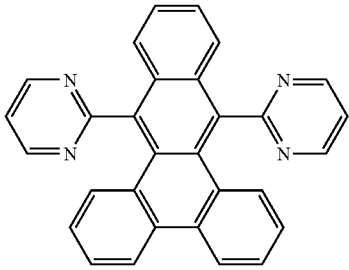
A14

A15
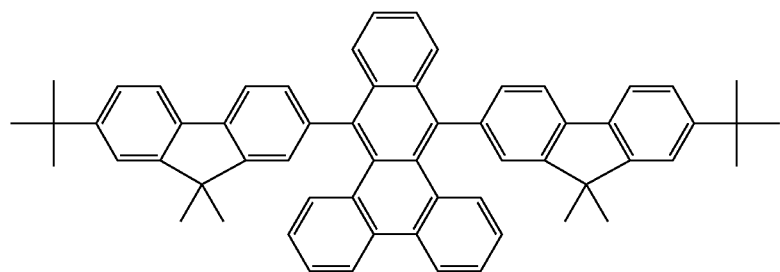
A16
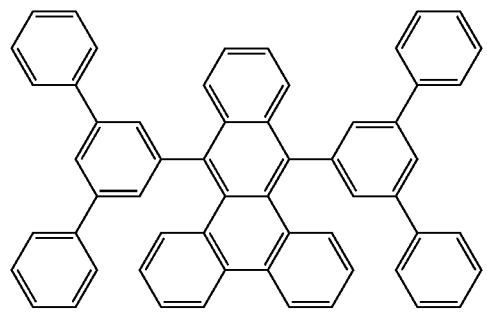
A17
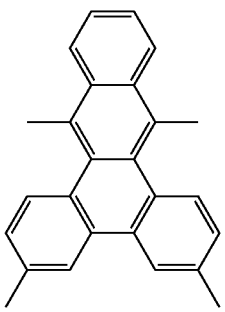
A18
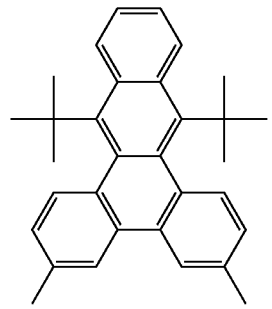
A19
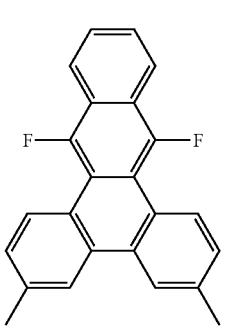
A20
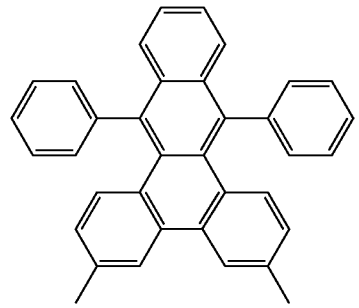
A21
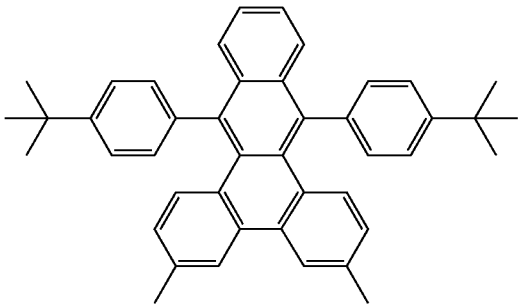
A22
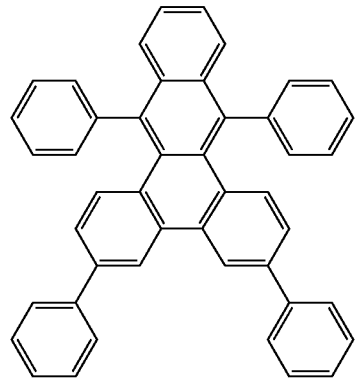
A23
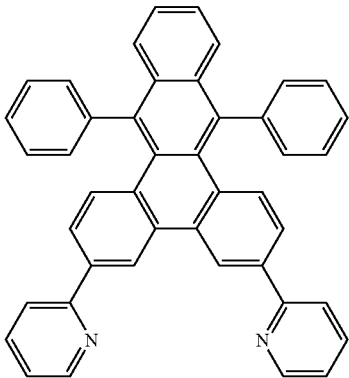

-continued
A24
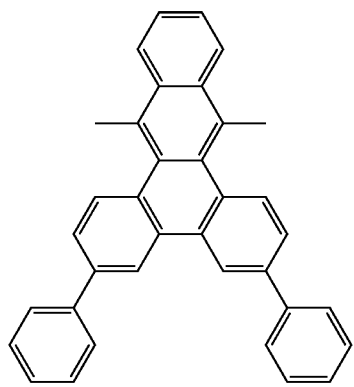
A25
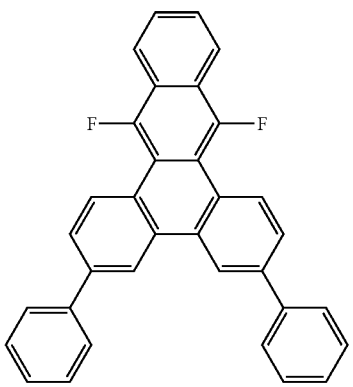
A26
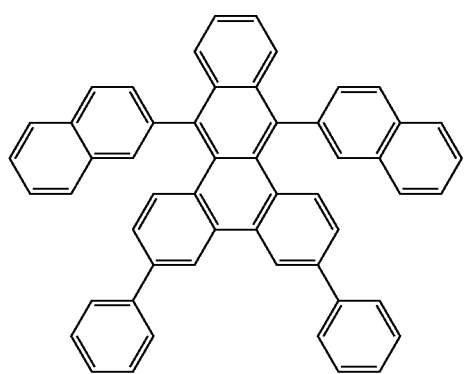
A27
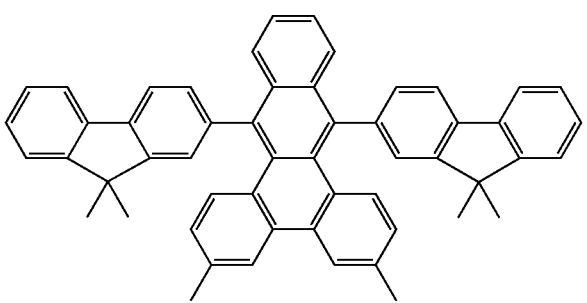
A28
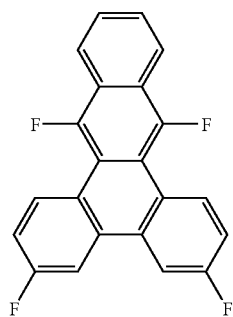
A29
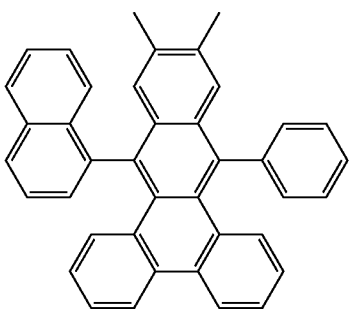
A30
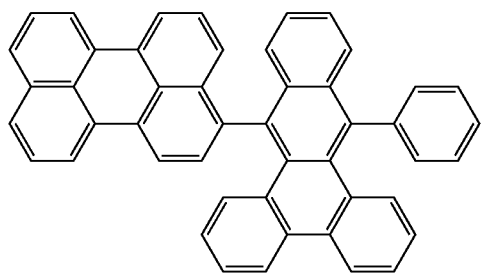
A31
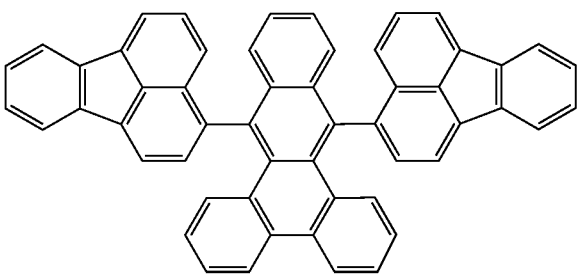

-continued
A32
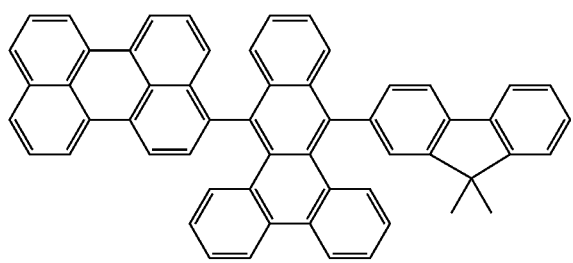
A33
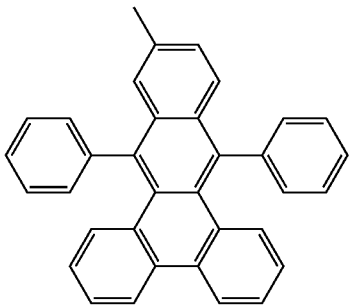
A34
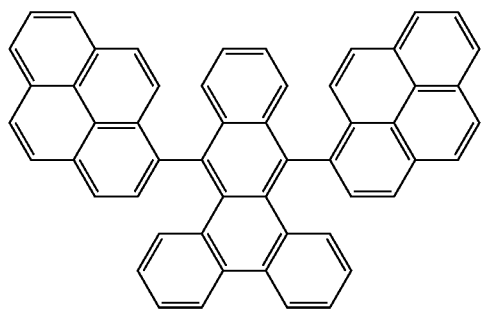
A35
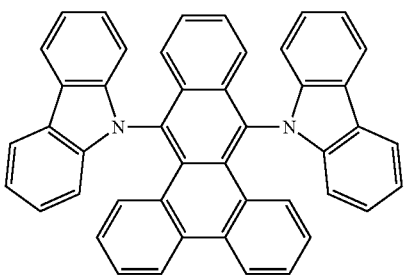
A36
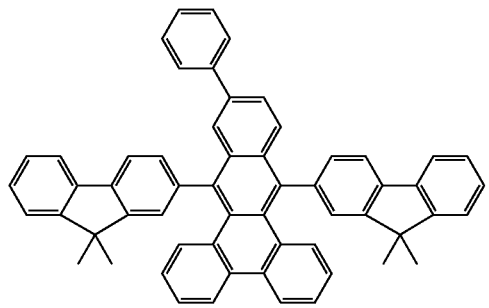
A37
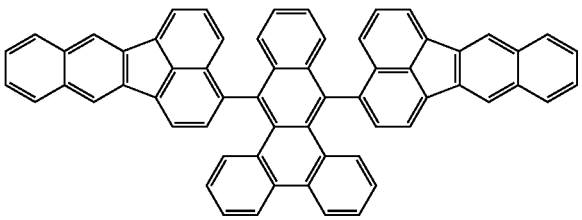
A38
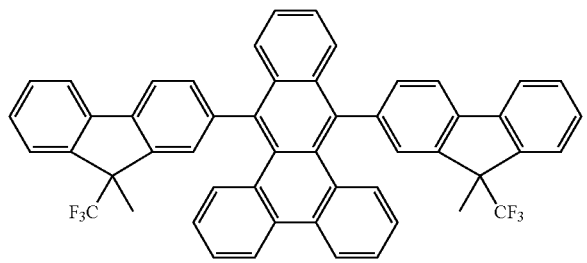
A39
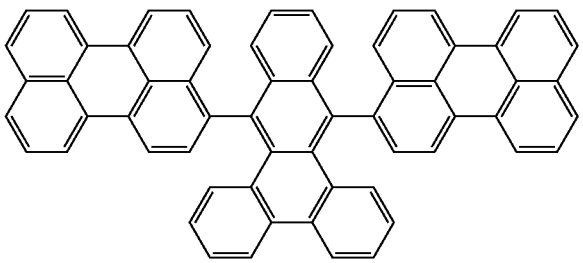
A40
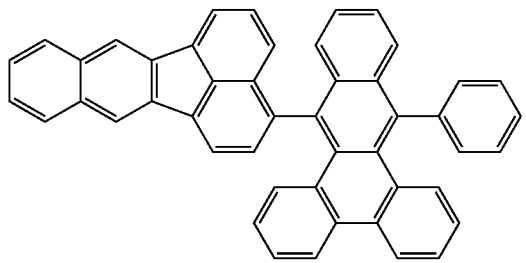
A41
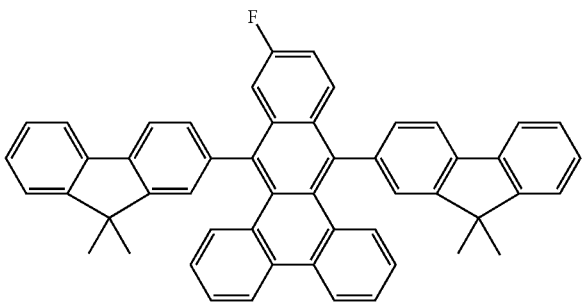

Next, an organic light emitting device of the present invention will be described.

The organic light emitting device has an anode, a cathode, and an organic layer interposed between the anode and the cathode.

The organic layer has the dibenzoanthracene compound according to the present invention. To be additionally specific, the organic layer itself may be a layer formed of the dibenzoanthracene compound according to the present invention, or the organic layer may be a layer containing the dibenzoanthracene compound according to the present invention.

When the organic layer is an organic layer containing the dibenzoanthracene compound according to the present invention, the dibenzoanthracene compound may be a main component (host material) or accessory component (guest material) of which the organic layer is formed.

When the dibenzoanthracene compound according to the present invention is a guest material, the compound accounts for preferably 50 wt % or less, more preferably 0.1 wt % or more to 30 wt % or less, or particularly preferably 0.1 wt % or more to 15 wt % or less of the organic layer.

Further, when the dibenzoanthracene compound according to the present invention is a guest material, the organic layer may contain another compound.

The organic layer is preferably a light emitting layer. Alternatively, the organic layer may be a layer except a light emitting layer which does not emit light.

A layer except the organic layer may be interposed between the anode and the cathode. When the organic layer formed of (or containing) the dibenzoanthracene compound according to the present invention is a light emitting layer, the term "layer except the organic layer" refers to a hole injecting layer, a hole transporting layer, an electron blocking layer, a hole blocking layer, an electron transporting layer, or an electron injecting layer.

Each of those layers may be appropriately provided in consideration of a light emission hue. Alternatively, each of the layers may be appropriately provided so that the functions of the layers may be separated from each other, that is, each of a carrier injecting ability, a carrier transporting ability, and a light emitting ability may be assigned.

Each layer except the organic layer may be formed only of an organic compound, may be formed only of an inorganic compound, or may be formed of both an organic compound and an inorganic compound.

The organic layer containing the dibenzoanthracene compound according to the present invention and any layer except the organic layer each have only to be appropriately formed by a preferable method. Specific examples of such method include a vapor deposition method and an application method.

Each of the anode and the cathode has only to be appropriately selected. For example, it is sufficient that one of the cathode and the anode is used as a light extraction electrode, and the other is used as an electrode placed on a side on which spontaneously emitted light is reflected.

In addition, a protective layer for protecting the organic light emitting device from external oxygen or moisture, or an external stress may be provided.

The organic light emitting device of the present invention may be placed on a display portion. In this case, a display apparatus having the organic light emitting device and a driver for controlling whether or not the organic light emitting device emits light can be provided. The driver is used for driving the organic light emitting device, and an example of the driver is a switching device, additionally specifically, a TFT.

The organic light emitting device of the present invention is applicable also to an exposure light source for a photosensitive member of an electrophotographic image forming device.

EXAMPLE 1

Synthesis of Exemplified Compound No. A-7

(1-1) Synthesis of Synthesis Intermediate Compound 3

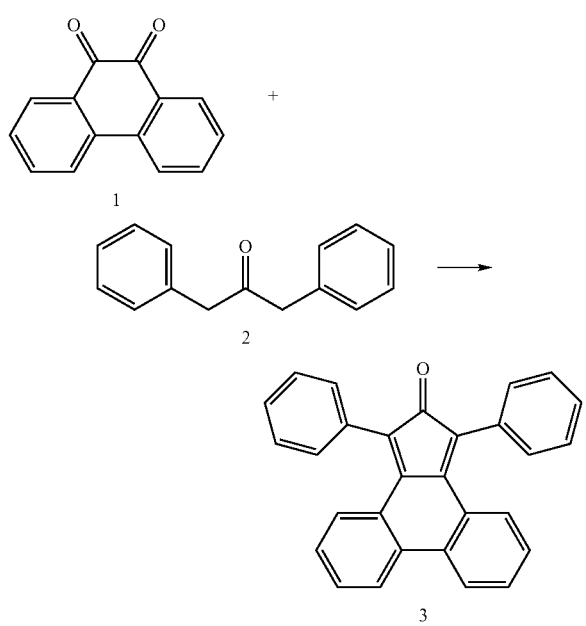

Compound 1 (7 g, 32.4 mmol), Compound 2 (7.5 g, 35.7 mmol), and 150 ml of ethanol were added to a 500-ml reaction vessel. 10 ml of ethanol in which KOH (2 g) had been dissolved were dropped to the solution at room temperature. After the complete dissolution of Compound 1 had been confirmed, the reaction vessel was placed in an oil bath at 80° C., and, furthermore, 10 ml of ethanol in which KOH (2 g) had been dissolved were dropped to the resultant. After the completion of the dropping, the reaction solution was stirred for about 5 minutes, and was then cooled with ice. After that, the precipitated crystal was filtrated and recrystallized, whereby Synthesis Intermediate Compound 3 was obtained (7.4 g, yield=60%).

(1-2) Synthesis of Exemplified Compound No. A-7

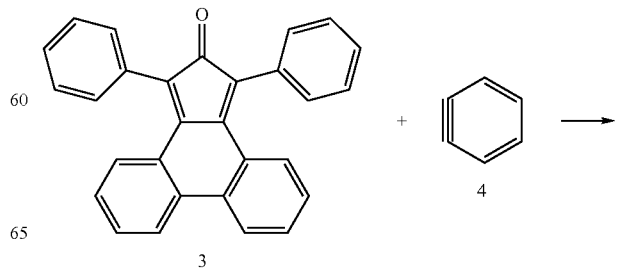

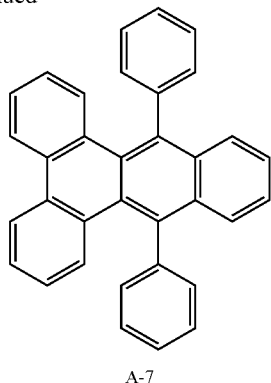

A-7

Under argon, Synthesis Intermediate Compound 3 (5 g, 13 mmol), and benzenediazonium-2-carboxylate hydrochloride (2.4 g, 13 mmol) and propylene oxide (2.8 g, 48 mmol) for producing Compound 4 were added to 1,2-dichloroethane (100 mL) in a 500-mL reaction vessel. The mixed liquid was refluxed under argon for 5 hours. After having been cooled, the solution was diluted with 100 ml of chloroform, and the resultant was washed with a saturated aqueous solution of sodium hydrogen carbonate (200 mL×twice). An organic layer was collected, washed with a saturated salt solution, and dried with anhydrous MgSO4. After that, the solution was condensed and purified by means of silica gel chromatography (hexane/toluene). After that, the resultant was recrystallized, whereby Exemplified Compound No. A-7 was obtained (2.4 g, yield=48%).

Matrix-assisted laser desorption/ionization time-of-flight mass spectrometry (MALDI-TOF MS) confirmed that the compound had an M+ of 430.

In addition, the structure of the compound was identified by NMR measurement.

$^1$H NMR (CDCl$_3$, 400 MHz) δ (ppm): 8.27 (dd, 2H), 7.93 (m, 2H), 7.57-7.49 (m, 12H), 7.48-7.43 (m, 2H), 7.34 (t, 2H), 6.97 (t, 2H)

EXAMPLE 2

Synthesis of Exemplified Compound No. A-10

Exemplified Compound No. A-10 can be synthesized by the same synthesis method as that of Example 1 except that Compound 5 is used instead of Compound 2.

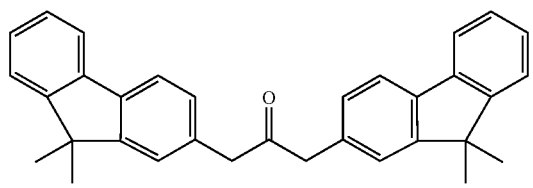

5

EXAMPLE 3

Synthesis of Exemplified Compound No. A-23

Exemplified Compound No. A-23 can be synthesized by the same synthesis method as that of Example 1 except that Compound 6 is used instead of Compound 2.

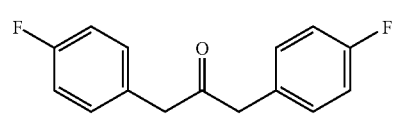

6

EXAMPLE 4

Synthesis of Exemplified Compound No. A-12

Exemplified Compound No. A-12 can be synthesized by the same synthesis method as that of Example 1 except that Compound 8 is used instead of Compound 2.

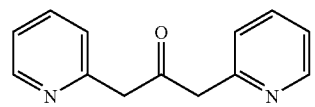

8

EXAMPLE 5

Synthesis of Exemplified Compound No. A-35

Exemplified Compound No. A-35 can be synthesized by the same synthesis method as that of Example 1 except that Compound 9 is used instead of Compound 2.

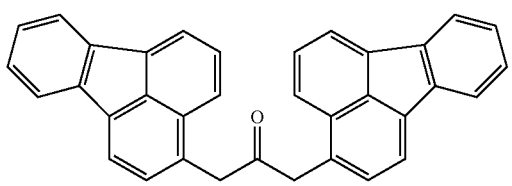

9

EXAMPLE 6

As the anode, a film of indium tin oxide (ITO) having a thickness of 120 nm was formed on a glass substrate by a sputtering method, and the resultant was used as a transparent conductive supporting substrate. The resultant substrate was sequentially subjected to ultrasonic cleaning in acetone and isopropyl alcohol (IPA). Then, the substrate was washed in boiling IPA and dried. The substrate was further subjected to UV/ozone cleaning to be used as a transparent conductive supporting substrate.

A chloroform solution of a compound represented by Compound B2 shown below was formed into a film having a thickness of 20 nm by a spin coating method on the transparent conductive supporting substrate, whereby a hole transporting layer was formed.

Further, the following organic layers and electrode layers were continuously formed by vacuum deposition based on resistance heating in a vacuum chamber having a pressure of 10$^{-5}$ Pa, whereby a device was produced.

Light emitting layer (20 nm): Exemplified Compound No. A-7 (2% in weight ratio): Compound B1

Electron transporting layer (30 nm): Bphen (manufactured by DOJINDO LABORATORIES)

Metal electrode layer 1 (0.5 nm): LiF
Metal electrode layer 2 (150 nm): Al

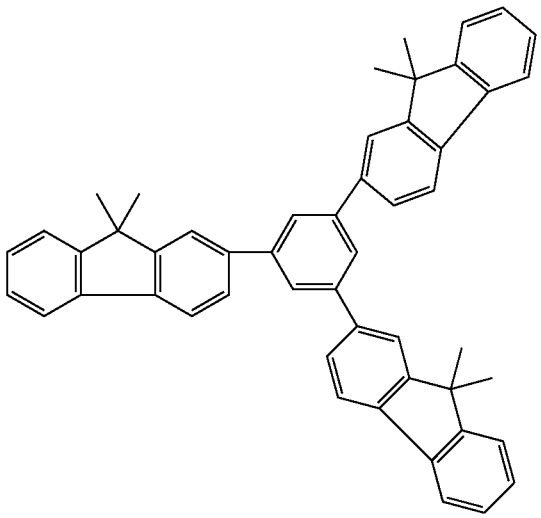

B1

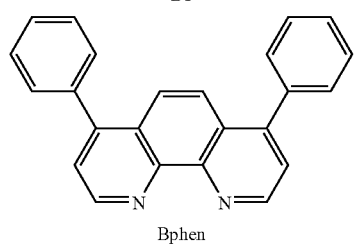

Bphen

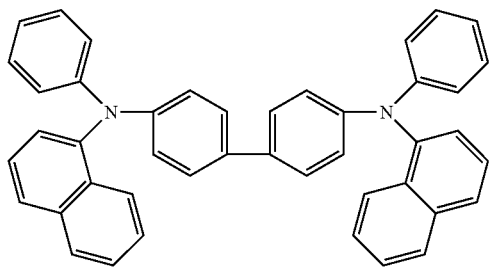

B2

The current-voltage characteristics of the resultant EL device were measured with a microammeter 4140 B manufactured by Hewlett-Packard Company, and the light emitting luminance of the device was measured with a BM 7 manufactured by TOPCON CORPORATION, whereby light emission was observed.

Further, a voltage was applied to the device for 100 hours under a nitrogen atmosphere. As a result, the device was observed to emit light in a favorable manner continuously.

As described above, the production of a light emitting device using a dibenzo[a,c]anthracene compound having substituents at both $R_1$ and $R_2$ was attained.

This application claims the benefit of Japanese Patent Application No. 2006-116903, filed Apr. 20, 2006, and Japanese Patent Application No. 2007-040900, filed Feb. 21, 2007, which are hereby incorporated by reference herein in their entirety.

The invention claimed is:

1. An electrophotographic image forming device comprising:
   a photosensitive member; and
   an exposure light source,
   wherein the exposure light source comprises an organic light emitting device to expose the photosensitive member, and
   wherein the organic light emitting device comprises an anode, a cathode and an organic light-emitting layer,
   wherein the organic light-emitting layer comprises a dibenzoanthracene compound that emits light and that is represented by the following structural formula (I):

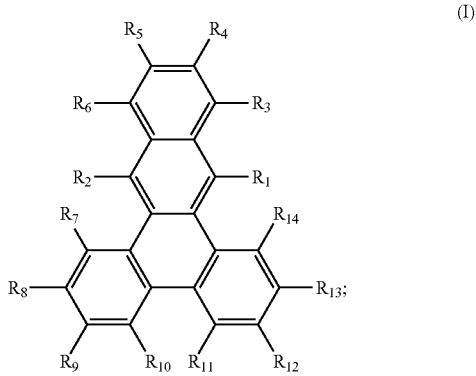

(I)

wherein both $R_1$ and $R_2$ represent a substituted or unsubstituted aryl group with the proviso that the substituted or unsubstituted aryl group does not contain a nitrogen atom, where the aryl group is any one of a phenyl group, a naphthyl group, a fluorenyl group, a phenanthryl group, and a perylenyl group;
wherein $R_3$ to $R_{14}$ each represent a hydrogen atom or a substituent; and
wherein the substituent represented by any one of $R_3$ to $R_{14}$ comprises any one of a straight or branched alkyl group in which a hydrogen atom may be substituted by a fluorine atom, a substituted or unsubstituted aryl group, where the aryl group is any one of a phenyl group, a naphthyl group, a fluorenyl group, a phenanthryl group, and a perylenyl group, a substituted or unsubstituted heterocyclic group, a substituted amino group, and a halogen atom.

2. The electrophotographic image forming device according to claim 1, wherein the dibenzoanthracene compound is represented by the following structural formula (II):

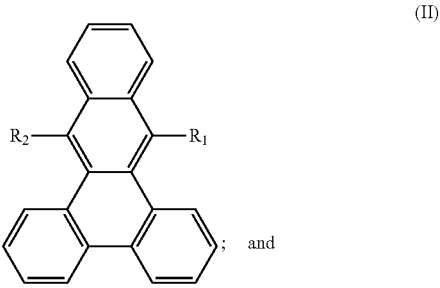

(II)

; and wherein both $R_1$ and $R_2$ represent a substituted or unsubstituted aryl group, where the aryl group is any one of a phenyl group, a naphthyl group, a fluorenyl group, a phenanthryl group, and a perylenyl group.

3. The electrophotographic image forming device according to claim 2, wherein both $R_1$ and $R_2$ are the substituted or unsubstituted phenyl group.

4. The electrophotographic image forming device according to claim 1, wherein $R_1$ and $R_2$ each represent a substituent consisting of carbon atoms and hydrogen atoms.

* * * * *